(12) United States Patent
Kim et al.

(10) Patent No.: US 11,293,014 B2
(45) Date of Patent: Apr. 5, 2022

(54) MICROORGANISM FOR PRODUCING L-AMINO ACID WITH ENHANCED ACTIVITY OF α-GLUCOSIDASE AND METHOD FOR PRODUCING L-AMINO ACID USING THE SAME

(71) Applicant: CJ CHEILJEDANG CORPORATION, Seoul (KR)

(72) Inventors: Kyungrim Kim, Seoul (KR); Hyo Jeong Byun, Suwon-si (KR); Kwang Woo Lee, Suwon-si (KR); Hyung Joon Kim, Seoul (KR); Yong Uk Shin, Yongin-si (KR); Jung Kee Lee, Daejeon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 16/484,315

(22) PCT Filed: Apr. 9, 2019

(86) PCT No.: PCT/KR2019/004228
§ 371 (c)(1),
(2) Date: Aug. 7, 2019

(87) PCT Pub. No.: WO2020/067618
PCT Pub. Date: Apr. 2, 2020

(65) Prior Publication Data
US 2021/0017510 A1 Jan. 21, 2021

(30) Foreign Application Priority Data
Sep. 28, 2018 (KR) .......................... 10-2018-0116540

(51) Int. Cl.
| | |
|---|---|
| C12N 9/26 | (2006.01) |
| C12N 1/20 | (2006.01) |
| C12P 13/04 | (2006.01) |
| C12P 13/06 | (2006.01) |
| C12P 13/08 | (2006.01) |

(52) U.S. Cl.
CPC .............. *C12N 9/2408* (2013.01); *C12N 1/20* (2013.01); *C12P 13/04* (2013.01); *C12P 13/06* (2013.01); *C12P 13/08* (2013.01); *C12Y 302/0102* (2013.01)

(58) Field of Classification Search
CPC ......... C12N 9/2408; C12N 1/20; C12P 13/08; C12P 13/04; C12P 13/06; C12Y 302/0102
See application file for complete search history.

(56) References Cited

U.S. PATENT DOCUMENTS

| | | |
|---|---|---|
| 9,228,215 B2 | 1/2016 | Takeshita et al. |
| 2014/0080185 A1 | 3/2014 | Takeshita et al. |

FOREIGN PATENT DOCUMENTS

| | | |
|---|---|---|
| EP | 2 241 632 A1 | 10/2010 |
| EP | 3 415 622 A1 | 12/2018 |
| KR | 10-0838038 B1 | 6/2008 |
| KR | 10-1484108 B1 | 1/2015 |
| KR | 10-1592140 B1 | 2/2016 |

OTHER PUBLICATIONS

Hermans et al., Human Mutation 23:47-56, 2004.*
Witkowski et al., Biochemistry 38:11643-11650, 1999.*
Tang et al., Phil Trans R Soc B 368:20120318, 1-10, 2013.*
Seffemick et al., J. Bacteriol. 183(8):2405-2410, 2001.*
Branden et al., Introduction to Protein Structure, Garland Publishing Inc., New York, p. 247, 1991.*
Sadowski et al. Current Opinion in Structural Biology 19:357-362, 2009.*
Van den Broek et al., Appl. Microbiol. Biotechnol. 61:55-60, 2003.*
Smirnov et al., Uchebnoe posobie "Fermenty. Klassifikatsiia i nomenklatura," Part III, 2008, Samara, Samarskii gosudarstvennyi tekhnicheskii universitet, p. 20-21 (with English translation of relevant portion).
NCBI Reference Sequence WP_004164340.1, alpha-glucosidase [Erwinia amylovora] (Jun. 7, 2016).
NCBI Reference Sequence NP_011803.3, oligo-1,6-glucosidase IMA1 [*Saccharomyces cerevisiae* S288C] (Mar. 15, 2017).
NCBI Reference Sequence WP_011743867.1, alpha-glucosidase [Bifidobacterium adolescentis] (Sep. 26, 2017).
GenBank: AP009256.1, "Bifidobacterium adolescentis ATCC 15703 DNA, complete genome," (353 pages) May 10, 2017.
Abe et al., "Engineering of *Escherichia coli* to facilitate efficient utilization of isomaltose and panose in industrial glucose feedstock," *Appl Microbriol Biotechnol* 707:2057-2066 (2017).
Anusree et al., "Co-expression of endoglucanase and β-glucosidase in *Corynebacterium glutamicum* DM1729 towards direct lysine fermentation for cellulose," *Bioresource Technology* 273:239-244 (2016).

* cited by examiner

*Primary Examiner* — Delia M Ramirez
(74) *Attorney, Agent, or Firm* — Seed IP Law Group LLP

(57) ABSTRACT

The present disclosure relates to a microorganism for producing an L-amino acid with enhanced activity of α-glucosidase and a method for producing an L-amino acid using the same. According to the present disclosure, the microorganism of the genus *Corynebacterium* producing an L-amino acid has enhanced activity of α-glucosidase, thereby improving L-amino acid production yield. Therefore, the microorganism may be very usefully used for L-amino acid production.

9 Claims, 1 Drawing Sheet
Specification includes a Sequence Listing.

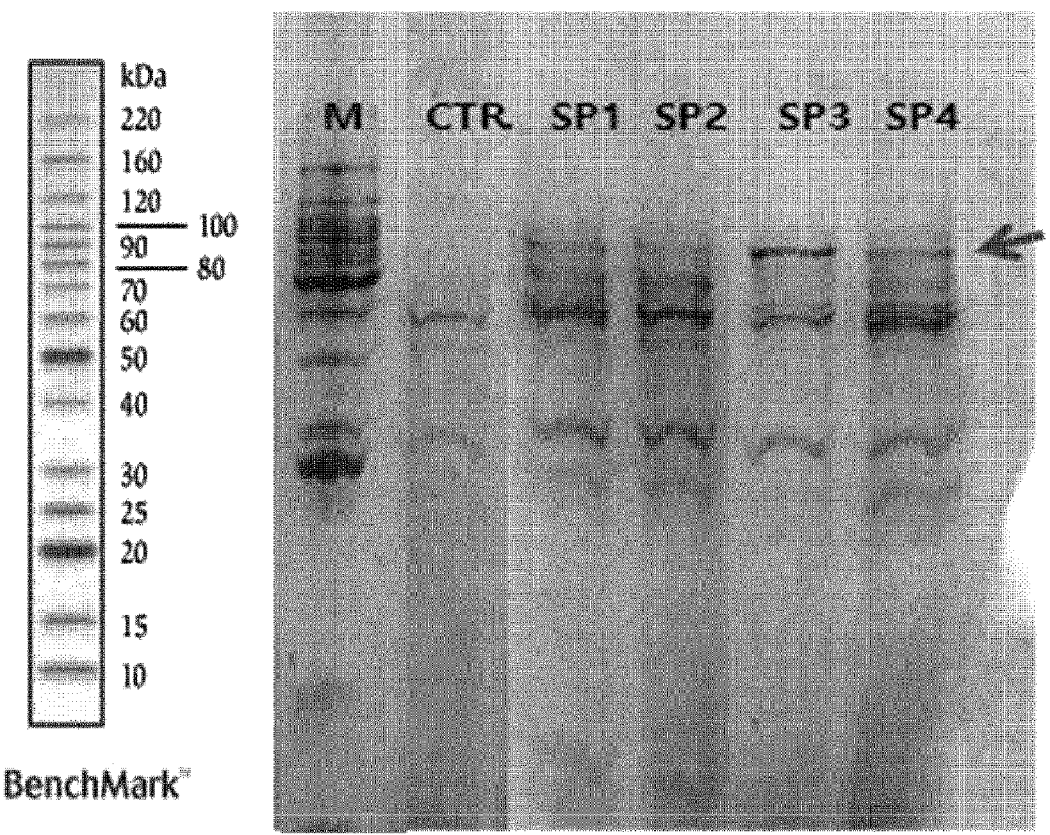

SEQUENCE LISTING

```
<160> NUMBER OF SEQ ID NOS: 31

<210> SEQ ID NO 1
<211> LENGTH: 606
<212> TYPE: PRT
<213> ORGANISM: Artificial Sequence
```

<220> FEATURE:
<223> OTHER INFORMATION: aglA from Bifidobacterium adolescentis

<400> SEQUENCE: 1

Met Thr Asn Phe Asn Arg Ser Thr Leu Ser Asp Thr Val Arg Ser Asn
1               5                   10                  15

Gly Ala Thr Pro Asn Pro Trp Trp Ala Asn Ala Val Val Tyr Gln Ile
                20                  25                  30

Tyr Pro Arg Ser Phe Gln Asp Ser Asn Gly Asp Gly Ile Gly Asp Leu
            35                  40                  45

Lys Gly Ile Thr Ser Arg Leu Asp Tyr Leu Ala Asp Leu Gly Val Asp
50                  55                  60

Val Leu Trp Leu Ser Pro Val Phe Lys Ser Pro Gln Asp Asp Asn Gly
65                  70                  75                  80

Tyr Asp Ile Ser Asp Tyr Gln Asp Ile Asp Pro Leu Phe Gly Thr Met
                85                  90                  95

Ala Asp Met Asp Glu Leu Leu Ala Glu Ala His Lys Arg Gly Leu Lys
            100                 105                 110

Val Ile Met Asp Leu Val Val Asn His Thr Ser Asp Glu His Ala Trp
        115                 120                 125

Phe Gln Ala Ser Arg Asp Lys Asn Asp Pro His Ala Asp Trp Tyr Trp
    130                 135                 140

Trp Arg Pro Ala Lys Pro Gly His Glu Pro Gly Thr Pro Gly Ala Glu
145                 150                 155                 160

Pro Asn Gln Trp Gly Ser Tyr Phe Gly Gly Ser Ala Trp Glu Tyr Asp
                165                 170                 175

Pro Lys Arg Gly Glu Tyr Phe Phe His Gln Tyr Ser Lys Lys Gln Pro
            180                 185                 190

Asp Leu Asn Trp Glu Asn Pro Glu Val Arg Lys Ala Val Tyr Lys Met
        195                 200                 205

Met Asn Trp Trp Met Asp Arg Gly Ile Asp Gly Phe Arg Met Asp Val
    210                 215                 220

Ile Thr Gln Ile Ser Lys Val Ile Asp Lys Asn Gly Lys Leu Pro Gly
225                 230                 235                 240

Glu Ala Gly Ser Glu Ile Ala Asp Asn Pro Val Gly Glu Gly Gly Tyr
                245                 250                 255

Ser Ser Pro Tyr Pro Phe Cys Ser Asp Gly Pro Arg Ile Asp Glu Phe
            260                 265                 270

Leu Ala Glu Met Arg Arg Glu Val Phe Glu Gly Arg Glu Gly Tyr Met
        275                 280                 285

Asn Val Gly Glu Ala Pro Gly Ile Thr Pro Ala Arg Asn Glu His Val
    290                 295                 300

Thr Asp Pro Ala Asn Lys Glu Leu Asp Met Leu Phe Leu Phe Asp His
305                 310                 315                 320

Val Gly Ile Asp Gln Glu Gly Ser Lys Trp Asn Thr Val Pro Phe Glu
                325                 330                 335

Val Lys Asn Leu Arg Asp Arg Met Thr Glu Gln Gln Glu Ala Val Arg
            340                 345                 350

Lys Ala Gly Trp Ala Ser Leu Phe Phe Cys Asn His Asp Gln Pro Arg
        355                 360                 365

Val Val Ser Arg Trp Gly Asn Asp Ser Asp Arg Asp Ser Arg Glu Leu
    370                 375                 380

Ser Ala Lys Ala Phe Gly Met Val Leu His Met His Arg Gly Thr Pro
385                 390                 395                 400

```
Tyr Ile Tyr Glu Gly Glu Glu Leu Gly Met Thr Asn Ala His Phe Thr
                405                 410                 415
Lys Leu Glu Gln Tyr Arg Asp Leu Glu Ala Leu Asn Gly Tyr Arg Gln
            420                 425                 430
Arg Val Glu Glu Ala Lys Cys Gln Ser Ser Glu Ser Met Met Ala Ala
        435                 440                 445
Leu Ala Leu Ile Gly Arg Asp Asn Ala Arg Thr Pro Met Gln Trp Asp
    450                 455                 460
Ala Ser Lys Tyr Ala Gly Phe Thr Pro Ala Asp Ala Ala Glu Pro
465                 470                 475                 480
Trp Ile Ser Val Asn Pro Asn His Val Glu Ile Asn Ala Ala Glu Glu
                485                 490                 495
Phe Asp Asp Pro Asp Ser Val Tyr Thr Phe Tyr Lys Lys Leu Ile Ala
            500                 505                 510
Met Arg His Asn Ser Ala Thr Ile Ser Thr Gly Glu Trp His Leu Leu
        515                 520                 525
Ala Ala Asp Ser Asp Gln Val Tyr Ala Phe Thr Arg Thr Asn Gly Asp
    530                 535                 540
Asp Thr Ile Leu Val Val Asn Leu Thr Asp Arg Ser Ala Ala Leu
545                 550                 555                 560
Pro Ser Asp Val Ala Glu Leu Leu Ser Asp Gly Val Ser Asp Pro Gln
                565                 570                 575
Val Leu Leu Ser Thr Tyr Asp Ala Met His Ser Val Lys Ser Ile Ala
            580                 585                 590
Arg Gly Glu Leu Ala Arg Trp Glu Gly Val Val Ile Gln Leu
        595                 600                 605

<210> SEQ ID NO 2
<211> LENGTH: 1821
<212> TYPE: DNA
<213> ORGANISM: Artificial Sequence
<220> FEATURE:
<223> OTHER INFORMATION: aglA from Bifidobacterium adolescentis

<400> SEQUENCE: 2
atgacgaatt tcaatcgttc cactctttct gacaccgtcc gttcgaatgg cgccaccccg      60
aatccgtggt gggcgaacgc ggtggtctac cagatctatc ccgttccttc caggattcc     120 aatggcgatg catcggcga tctgaagggc atcaccagcc ggctcgacta tctcgcagat     180
ctcggcgtgg acgtgctatg ctgtccccg gtcttcaagt ccccgcagga cgacaacggc     240
tacgacatct ccgactacca ggacatcgat ccgctgttcg gcacaatggc cgatatggac     300
gagctgcttg ccgaagcgca caagcgcggc ctgaaggtca tcatggacct ggtcgtgaac     360
cacacgtccg acgagcatgc ctggttccag gcttcccgcg acaagaacga tcctcatgcg     420
gattggtatt ggtggcgtcc ggccaagccg ggccatgagc cgggcacgcc cggtgccgag     480
ccgaaccagt ggggctccta tttcggcggc tccgcatggg agtacgatcc gaagcgcggt     540
gaatacttct tcaccagta ttccaagaag cagcccgacc tcaactggga gaatcccgag     600
gtgcgcaagg ccgtctacaa gatgatgaac tggtggatgg atcgcggcat cgacggcttc     660
cgcatggacg tgatcaccca gatttccaag gtcatcgaca gaacggcaa gttgccgggg     720 gaggcaggat ccgaaatcgc cgataatccg gttggagagg aaggttattc cagcccgtat     780
ccgttctgct ccgacggccc cgcatcgac gagttcctcg ccgaaatgcg ccgtgaggta     840
ttcgaaggcc gtgaaggcta catgaatgtc ggcgaggctc cgggcatcac cccggcccgt     900
```

```
aacgagcacg tcaccgatcc ggccaacaag gaacttgaca tgctattcct gtttgaccat    960
gtcggcatcg accaggaagg ctccaagtgg aataccgtgc cgttcgaggt caaaaacctg   1020
cgcgaccgta tgaccgagca gcaggaggcc gtgaggaagg ccggttgggc cagcctgttc   1080
ttctgcaatc atgaccagcc gcgcgtggtc tcccgttggg caacgactc cgaccgcgat    1140 tcgcgcgaac tgagcgccaa ggcgttcggc atggtgctgc acatgcaccg cggcaccccg   1200
tacatttacg aaggcgagga actgggtatg accaacgccc acttcaccaa gctggaacaa   1260
taccgcgatc tggaagccct caacggctat cgccagcgcg tggaggaagc caagtgccag   1320
tcgtccgaat ccatgatggc cgccctcgcc ctcatcggcc gcgacaacgc gcgcaccccc   1380
atgcagtggg acgcctccaa gtatgccggt ttcaccccgg cggacgcggc agccgaaccg   1440
tggatcagcg tcaacccgaa tcatgtggaa atcaacgcgg ccgaggaatt cgacgatccg   1500
gattccgtgt acacgttcta caagaagctc atcgccatgc ggcacaacag cgccaccatc   1560
tccactggcg aatggcatct gctcgccgcc gacagcgatc aggtgtatgc tttcacgcgc   1620
accaatggcg acgacgat tcttgtcgtg gtcaacctca ccgacaggtc cgcggcgctg     1680
ccttcggacg tggcggagct gctttccgac ggcgtgtccg atccgcaagt actgctcagc   1740
acctatgatg ctatgcatag tgttaaatcg atcgctcgtg gcgagctcgc tcgctgggag   1800
ggagtcgtga ttcagctctg a                                             1821

<210> SEQ ID NO 3
<211> LENGTH: 29
<212> TYPE: DNA
<213> ORGANISM: Artificial Sequence
<220> FEATURE:
<223> OTHER INFORMATION: PgapA-F

<400> SEQUENCE: 3
tcagaattct tgggattacc attgaagcc                                       29

<210> SEQ ID NO 4
<211> LENGTH: 29
<212> TYPE: DNA
<213> ORGANISM: Artificial Sequence
<220> FEATURE:
<223> OTHER INFORMATION: PgapA-R

<400> SEQUENCE: 4
tcacatatgg tgtctcctct aaagattgt                                       29

<210> SEQ ID NO 5
<211> LENGTH: 124
<212> TYPE: DNA
<213> ORGANISM: Artificial Sequence
<220> FEATURE:
<223> OTHER INFORMATION: aglA ORF SP1-F for amplification

<400> SEQUENCE: 5
tcacatatgc aaataaaccg ccgaggcttc ttaaaagcca ccgcaggact tgccactatc     60
ggcgctgcca gcatgtttat gccaaaggcc aacgcccttg agcaacgaa tttcaatcgt    120 tcca                                                                124

<210> SEQ ID NO 6
<211> LENGTH: 148
<212> TYPE: DNA
<213> ORGANISM: Artificial Sequence
<220> FEATURE:
<223> OTHER INFORMATION: aglA ORF SP2-F for amplification
```

<400> SEQUENCE: 6
tcacatatgc attcaaagga agagttaaca gtgcgtaaag gaatttcccg cgtcctctcg    60
gtagcggttg ctagttcaat cggattcgga actgtactga caggcaccgg catcgcagca   120
gctcaagaca cgaatttcaa tcgttcca                                      148

<210> SEQ ID NO 7
<211> LENGTH: 115
<212> TYPE: DNA
<213> ORGANISM: Artificial Sequence
<220> FEATURE:
<223> OTHER INFORMATION: aglA ORF SP3-F for amplification

<400> SEQUENCE: 7
tcacatatgc gtaagttccg caatactgca atcgcactgg tttcagctgc tgctatctcc    60
ctcggtggag ttactgctgc aaccgctcag gaagctacga atttcaatcg ttcca        115

<210> SEQ ID NO 8
<211> LENGTH: 94
<212> TYPE: DNA
<213> ORGANISM: Artificial Sequence
<220> FEATURE:
<223> OTHER INFORMATION: aglA ORF SP4-F for amplification

<400> SEQUENCE: 8
tcacatatga aaagaatat cgcatttctt cttgcatcta tgttcgtttt ttctattgct    60
acaaacgcgt acgctacgaa tttcaatcgt tcca                                94

<210> SEQ ID NO 9
<211> LENGTH: 29
<212> TYPE: DNA
<213> ORGANISM: Artificial Sequence
<220> FEATURE:
<223> OTHER INFORMATION: aglA ORF-R for amplification

<400> SEQUENCE: 9
tcaactagtt cagagctgaa tcacgactc                                      29

<210> SEQ ID NO 10
<211> LENGTH: 116
<212> TYPE: DNA
<213> ORGANISM: Artificial Sequence
<220> FEATURE:
<223> OTHER INFORMATION: malL ORF SP3-F for amplification

<400> SEQUENCE: 10
tcacatatgc gtaagttccg caatactgca atcgcactgg tttcagctgc tgctatctcc    60
ctcggtggag ttactgctgc aaccgctcag gaagcttcag gcatcaaact ttcttc       116

<210> SEQ ID NO 11
<211> LENGTH: 29
<212> TYPE: DNA
<213> ORGANISM: Artificial Sequence
<220> FEATURE:
<223> OTHER INFORMATION: malL ORF-R for amplification

<400> SEQUENCE: 11
tcaactagtt caatttagcc tatagatac                                      29

<210> SEQ ID NO 12
<211> LENGTH: 116
<212> TYPE: DNA
<213> ORGANISM: Artificial Sequence
<220> FEATURE:
<223> OTHER INFORMATION: Ima1 ORF SP3-F for amplification

<400> SEQUENCE: 12
tcacatatgc gtaagttccg caatactgca atcgcactgg tttcagctgc tgctatctcc     60
ctcggtggag ttactgctgc aaccgctcag gaagctacta tttcttctgc acatcc        116

<210> SEQ ID NO 13
<211> LENGTH: 31
<212> TYPE: DNA
<213> ORGANISM: Artificial Sequence
<220> FEATURE:
<223> OTHER INFORMATION: Ima1 ORF-R for amplification

<400> SEQUENCE: 13
tcaactagtt cattcgctga tatatattct t                                    31

<210> SEQ ID NO 14
<211> LENGTH: 33
<212> TYPE: PRT
<213> ORGANISM: Artificial Sequence
<220> FEATURE:
<223> OTHER INFORMATION: SP1 (CgR0949)

<400> SEQUENCE: 14

Met Gln Ile Asn Arg Arg Gly Phe Leu Lys Ala Thr Ala Gly Leu Ala
1               5                   10                  15

Thr Ile Gly Ala Ala Ser Met Phe Met Pro Lys Ala Asn Ala Leu Gly
            20                  25                  30

Ala

<210> SEQ ID NO 15
<211> LENGTH: 41
<212> TYPE: PRT
<213> ORGANISM: Artificial Sequence
<220> FEATURE:
<223> OTHER INFORMATION: SP2 (NCgl2101)

<400> SEQUENCE: 15

Met His Ser Lys Glu Glu Leu Thr Val Arg Lys Gly Ile Ser Arg Val
1               5                   10                  15

Leu Ser Val Ala Val Ala Ser Ser Ile Gly Phe Gly Thr Val Leu Thr
            20                  25                  30

Gly Thr Gly Ile Ala Ala Ala Gln Asp
        35                  40

<210> SEQ ID NO 16
<211> LENGTH: 30
<212> TYPE: PRT
<213> ORGANISM: Artificial Sequence
<220> FEATURE:
<223> OTHER INFORMATION: SP3 (CgR1834)

<400> SEQUENCE: 16

Met Arg Lys Phe Arg Asn Thr Ala Ile Ala Leu Val Ser Ala Ala Ala
1               5                   10                  15

Ile Ser Leu Gly Gly Val Thr Ala Ala Thr Ala Gln Glu Ala
            20                  25                  30

<210> SEQ ID NO 17
<211> LENGTH: 23
<212> TYPE: PRT
<213> ORGANISM: Artificial Sequence -continued

<220> FEATURE:
<223> OTHER INFORMATION: SP4 (ST2)

<400> SEQUENCE: 17

Met Lys Lys Asn Ile Ala Phe Leu Leu Ala Ser Met Phe Val Phe Ser
1               5                   10                  15

Ile Ala Thr Asn Ala Tyr Ala
            20

<210> SEQ ID NO 18
<211> LENGTH: 21
<212> TYPE: DNA
<213> ORGANISM: Artificial Sequence
<220> FEATURE:
<223> OTHER INFORMATION: aglA-F for confirmation

<400> SEQUENCE: 18
gaccatttat tcgcaactgt g                                         21

<210> SEQ ID NO 19
<211> LENGTH: 20
<212> TYPE: DNA
<213> ORGANISM: Artificial Sequence
<220> FEATURE:
<223> OTHER INFORMATION: aglA-R for confirmation

<400> SEQUENCE: 19
tctgcaaggc gttcggaatt                                           20

<210> SEQ ID NO 20
<211> LENGTH: 29
<212> TYPE: DNA
<213> ORGANISM: Artificial Sequence
<220> FEATURE:
<223> OTHER INFORMATION: XbaI-F for insertion

<400> SEQUENCE: 20
tcctctagac tggtcgcctg atgttctac                                 29

<210> SEQ ID NO 21
<211> LENGTH: 29
<212> TYPE: DNA
<213> ORGANISM: Artificial Sequence
<220> FEATURE:
<223> OTHER INFORMATION: XbaI-R for insertion

<400> SEQUENCE: 21
gactctagat tagtcccttt cgaggcgga                                 29

<210> SEQ ID NO 22
<211> LENGTH: 20
<212> TYPE: DNA
<213> ORGANISM: Artificial Sequence
<220> FEATURE:
<223> OTHER INFORMATION: hom-F for substitution

<400> SEQUENCE: 22
gccaaaacct ccacgcgatc                                           20

<210> SEQ ID NO 23
<211> LENGTH: 20
<212> TYPE: DNA
<213> ORGANISM: Artificial Sequence
<220> FEATURE:
<223> OTHER INFORMATION: hom-R for substitution

<400> SEQUENCE: 23
atcgcgtgga ggttttggct                                                20

<210> SEQ ID NO 24
<211> LENGTH: 28
<212> TYPE: DNA
<213> ORGANISM: Artificial Sequence
<220> FEATURE:
<223> OTHER INFORMATION: XbaI-F for insertion (2)

<400> SEQUENCE: 24
acggatccca gactccaaag caaaagcg                                        28

<210> SEQ ID NO 25
<211> LENGTH: 28
<212> TYPE: DNA
<213> ORGANISM: Artificial Sequence
<220> FEATURE:
<223> OTHER INFORMATION: XbaI-R for insertion (2)

<400> SEQUENCE: 25
acggatccaa ccaaacttgc tcacactc                                        28

<210> SEQ ID NO 26
<211> LENGTH: 30
<212> TYPE: DNA
<213> ORGANISM: Artificial Sequence
<220> FEATURE:
<223> OTHER INFORMATION: ilvA-F for substitution

<400> SEQUENCE: 26
acaccacggc agaaccaggt gcaaaggaca                                      30

<210> SEQ ID NO 27
<211> LENGTH: 30
<212> TYPE: DNA
<213> ORGANISM: Artificial Sequence
<220> FEATURE:
<223> OTHER INFORMATION: ilvA-R for substitution

<400> SEQUENCE: 27
ctggttctgc cgtggtgtgc atcatctctg                                      30

<210> SEQ ID NO 28
<211> LENGTH: 599
<212> TYPE: PRT
<213> ORGANISM: Artificial Sequence
<220> FEATURE:
<223> OTHER INFORMATION: aglA from Erwinia amylovora

<400> SEQUENCE: 28

Met Ser Gly Ile Lys Leu Ser Ser Val Met Ala Leu Phe Phe Ala Pro
1               5                   10                  15

Phe Leu Ala Val Ser Ser Gly Gln Val Leu Ala Gly Lys Thr Asp Ile
                20                  25                  30

Ala Thr Thr Gln Val Val His Lys Ser Asp Asp Phe Pro Ala Trp Trp
        35                  40                  45

Lys Gln Ala Val Phe Tyr Gln Val Tyr Pro Arg Ser Phe Lys Asp Thr
    50                  55                  60

Asn Gly Asp Gly Ile Gly Asp Ile Lys Gly Ile Ile Glu Lys Leu Asp
65                  70                  75                  80

Tyr Leu Asn Asn Leu Gly Val Asp Ala Ile Trp Ile Asn Pro His Tyr
                85                  90                  95

```
Asp Ser Pro Asn Thr Asp Asn Gly Tyr Asp Ile Arg Asp Tyr Arg Lys
            100                 105                 110

Ile Met Lys Glu Tyr Gly Thr Met Glu Asp Phe Asp Arg Leu Ile Ala
        115                 120                 125

Glu Met Asn Lys Arg Asn Met Arg Leu Met Ile Asp Ile Val Ile Asn
    130                 135                 140

His Thr Ser Asp Gln His Arg Trp Phe Val Gln Ser Lys Ser Ser Lys
145                 150                 155                 160

Asp Asn Pro Tyr Arg Glu Tyr Tyr Phe Trp Arg Asp Gly Lys Asn Gly
                165                 170                 175

Gln Pro Pro Asn Asn Tyr Pro Ser Phe Phe Gly Gly Ser Ala Trp Glu
            180                 185                 190

Lys Glu Asp His Ser Gly Gln Tyr Tyr Leu His Tyr Phe Ala Lys Gln
        195                 200                 205

Gln Pro Asp Leu Asn Trp Asp Asn Pro Lys Val Arg Glu Asp Leu Tyr
    210                 215                 220

Ala Met Leu Arg Phe Trp Leu Asp Lys Gly Val Ala Gly Leu Arg Phe
225                 230                 235                 240

Asp Thr Val Ala Thr Tyr Ala Lys Ile Pro Asn Phe Pro Asp Leu Thr
                245                 250                 255

Pro Ser Gln Arg Gln Asn Phe Ala Arg Thr Tyr Thr Glu Gly Pro Ser
            260                 265                 270

Ile His Arg Tyr Ile Lys Glu Met Asn Arg Gln Val Phe Ser His Tyr
        275                 280                 285

Asn Ile Ala Thr Ala Gly Glu Ile Phe Gly Val Pro Leu Glu Lys Ser
    290                 295                 300

Ile Asn Tyr Phe Asp Arg Arg Asn Glu Leu Asn Ile Ala Phe Thr
305                 310                 315                 320

Phe Asp Leu Ile Arg Leu Asp Arg Asn Val Glu Glu Arg Trp Arg Glu
                325                 330                 335

Lys Ala Trp Ser Leu Val Asp Phe Arg Gln Thr Ile Gly Lys Val Asp
            340                 345                 350

Arg Ala Ala Gly Lys Tyr Gly Trp Asn Ala Phe Phe Leu Asp Asn His
        355                 360                 365

Asp Asn Pro Arg Ala Val Ser His Phe Gly Asp Asp Arg Pro Gln Trp
    370                 375                 380

Arg Gln Ala Ser Ala Lys Ala Leu Ala Thr Leu Ile Ile Thr Gln Arg
385                 390                 395                 400

Ala Thr Pro Phe Ile Tyr Gln Gly Ser Glu Leu Gly Met Thr Asn Tyr
                405                 410                 415

Pro Phe Lys Thr Ile Ala Asp Phe Asp Asp Ile Glu Val Lys Gly Phe
            420                 425                 430

Trp Gln Asp Tyr Val Ser Ser Gly Arg Val Asp Pro Glu Asp Phe Met
        435                 440                 445

Arg Asn Val Arg Leu Thr Ser Arg Asp Asn Ser Arg Thr Pro Phe Gln
    450                 455                 460

Trp Asp Glu Ser Ala His Ala Gly Phe Thr Ser Gly Thr Pro Trp Phe
465                 470                 475                 480

Lys Val Asn Pro Asn Tyr Lys Leu Ile Asn Ala Ser Asp Gln Met Lys
                485                 490                 495

Asp Ser Asp Ser Val Phe Asn Tyr Tyr Arg Lys Leu Ile Arg Leu Arg
            500                 505                 510
```

His Ala Ile Pro Ala Leu Thr Tyr Gly Glu Tyr Lys Asp Leu Asp Pro
                515                 520                 525

Tyr Asn Asp Thr Val Tyr Ala Phe Thr Arg Thr His Gly Asp Lys Arg
            530                 535                 540

Tyr Leu Val Val Ile Asn Phe Lys Glu Asn Lys Val Asn Tyr Arg Leu
545                 550                 555                 560

Pro Gly Gln Leu Ser Ile Arg Gln Thr Leu Ser Glu Ser Ser Ala Ser
                565                 570                 575

Gln Arg Val Ala Asp Asn Ala His Glu Leu Leu Leu Gln Pro Trp Gln
            580                 585                 590

Ser Gly Ile Tyr Arg Leu Asn
        595

<210> SEQ ID NO 29
<211> LENGTH: 589
<212> TYPE: PRT
<213> ORGANISM: Artificial Sequence
<220> FEATURE:
<223> OTHER INFORMATION: aglA from Saccharomyces cerevisiae

<400> SEQUENCE: 29

Met Thr Ile Ser Ser Ala His Pro Glu Thr Glu Pro Lys Trp Trp Lys
1               5                   10                  15

Glu Ala Thr Phe Tyr Gln Ile Tyr Pro Ala Ser Phe Lys Asp Ser Asn
            20                  25                  30

Asp Asp Gly Trp Gly Asp Met Lys Gly Ile Ala Ser Lys Leu Glu Tyr
        35                  40                  45

Ile Lys Glu Leu Gly Ala Asp Ala Ile Trp Ile Ser Pro Phe Tyr Asp
    50                  55                  60

Ser Pro Gln Asp Asp Met Gly Tyr Asp Ile Ala Asn Tyr Glu Lys Val
65                  70                  75                  80

Trp Pro Thr Tyr Gly Thr Asn Glu Asp Cys Phe Ala Leu Ile Glu Lys
                85                  90                  95

Thr His Lys Leu Gly Met Lys Phe Ile Thr Asp Leu Val Ile Asn His
            100                 105                 110

Cys Ser Ser Glu His Glu Trp Phe Lys Glu Ser Arg Ser Ser Lys Thr
        115                 120                 125

Asn Pro Lys Arg Asp Trp Phe Phe Trp Arg Pro Pro Lys Gly Tyr Asp
    130                 135                 140

Ala Glu Gly Lys Pro Ile Pro Pro Asn Asn Trp Lys Ser Tyr Phe Gly
145                 150                 155                 160

Gly Ser Ala Trp Thr Phe Asp Glu Lys Thr Gln Glu Phe Tyr Leu Arg
                165                 170                 175

Leu Phe Cys Ser Thr Gln Pro Asp Leu Asn Trp Glu Asn Glu Asp Cys
            180                 185                 190

Arg Lys Ala Ile Tyr Glu Ser Ala Val Gly Tyr Trp Leu Asp His Gly
        195                 200                 205

Val Asp Gly Phe Arg Ile Asp Val Gly Ser Leu Tyr Ser Lys Val Val
    210                 215                 220

Gly Leu Pro Asp Ala Pro Val Val Asp Lys Asn Ser Thr Trp Gln Ser
225                 230                 235                 240

Ser Asp Pro Tyr Thr Leu Asn Gly Pro Arg Ile His Glu Phe His Gln
                245                 250                 255

Glu Met Asn Gln Phe Ile Arg Asn Arg Val Lys Asp Gly Arg Glu Ile
            260                 265                 270

```
Met Thr Val Gly Glu Met Gln His Ala Ser Asp Glu Thr Lys Arg Leu
        275                 280                 285

Tyr Thr Ser Ala Ser Arg His Glu Leu Ser Glu Leu Phe Asn Phe Ser
    290                 295                 300

His Thr Asp Val Gly Thr Ser Pro Leu Phe Arg Tyr Asn Leu Val Pro
305                 310                 315                 320

Phe Glu Leu Lys Asp Trp Lys Ile Ala Leu Ala Glu Leu Phe Arg Tyr
                325                 330                 335

Ile Asn Gly Thr Asp Cys Trp Ser Thr Ile Tyr Leu Glu Asn His Asp
            340                 345                 350

Gln Pro Arg Ser Ile Thr Arg Phe Gly Asp Asp Ser Pro Lys Asn Arg
        355                 360                 365

Val Ile Ser Gly Lys Leu Leu Ser Val Leu Leu Ser Ala Leu Thr Gly
    370                 375                 380

Thr Leu Tyr Val Tyr Gln Gly Gln Glu Leu Gly Gln Ile Asn Phe Lys
385                 390                 395                 400

Asn Trp Pro Val Glu Lys Tyr Glu Asp Val Glu Ile Arg Asn Asn Tyr
                405                 410                 415

Asn Ala Ile Lys Glu Glu His Gly Glu Asn Ser Glu Glu Met Lys Lys
            420                 425                 430

Phe Leu Glu Ala Ile Ala Leu Ile Ser Arg Asp His Ala Arg Thr Pro
        435                 440                 445

Met Gln Trp Ser Arg Glu Glu Pro Asn Ala Gly Phe Ser Gly Pro Ser
    450                 455                 460

Ala Lys Pro Trp Phe Tyr Leu Asn Asp Ser Phe Arg Glu Gly Ile Asn
465                 470                 475                 480

Val Glu Asp Glu Ile Lys Asp Pro Asn Ser Val Leu Asn Phe Trp Lys
                485                 490                 495

Glu Ala Leu Lys Phe Arg Lys Ala His Lys Asp Ile Thr Val Tyr Gly
            500                 505                 510

Tyr Asp Phe Glu Phe Ile Asp Leu Asp Asn Lys Lys Leu Phe Ser Phe
        515                 520                 525

Thr Lys Lys Tyr Asn Asn Lys Thr Leu Phe Ala Ala Leu Asn Phe Ser
    530                 535                 540

Ser Asp Ala Thr Asp Phe Lys Ile Pro Asn Asp Asp Ser Ser Phe Lys
545                 550                 555                 560

Leu Glu Phe Gly Asn Tyr Pro Lys Lys Glu Val Asp Ala Ser Ser Arg
                565                 570                 575

Thr Leu Lys Pro Trp Glu Gly Arg Ile Tyr Ile Ser Glu
            580                 585
```

```
<210> SEQ ID NO 30
<211> LENGTH: 1800
<212> TYPE: DNA
<213> ORGANISM: Artificial Sequence
<220> FEATURE:
<223> OTHER INFORMATION: aglA from Erwinia amylovora

<400> SEQUENCE: 30
atgtcaggca tcaaactttc ttcagtcatg gcactcttct tcgccccatt tcttgctgtt      60
agttcaggtc aggtgctcgc aggaaagacg gatatcgcta ccacccaagt ggtgcataag     120
tccgatgact tcccggcatg gtggaagcaa gcggtgtttt accaggttta tccacgcagc     180
ttcaaagaca cgaacggtga tggtattggt gacattaagg gaatcatcga gaagctcgat     240
taccttaaca accttggcgt agatgcgatt tggattaacc cacactacga tagcccaaat     300
```

| | |
|---|---|
| actgacaacg gctacgatat tcgtgattac cgcaagatca tgaaagagta cggaaccatg | 360 |
| gaagatttcg atcgtttgat cgcagaaatg aataagcgta acatgcgcct catgatcgac | 420 |
| atcgttatca accacacttc tgaccagcac cgctggttcg tgcagagcaa gtcgtctaag | 480 |
| gataacccgt atcgcgaata ctactttggg cgcgatggaa agaacggcca accacctaac | 540 |
| aactatccgt ccttcttcgg tggttctgcg tgggaaaaag aggaccattc cgggcagtat | 600 |
| tatctacatt acttcgctaa acaacagcca gacctgaatt gggataaccc taaggttcgc | 660 |
| gaagatttgt acgcgatgct ccggttctgg ctcgacaaag gcgtcgctgg actgcggttc | 720 |
| gacaccgtag ccacctacgc taagatcccg aacttccctg acctcacgcc ctcgcaacga | 780 |
| cagaattttg cccgaactta taccgaaggt cccagtattc atcggtacat caaagaaatg | 840 |
| aacaggcaag tgttttctca ctacaatatc gctacagctg gggagatctt cggcgtcccg | 900 |
| ctggaaaagt cgattaacta tttcgaccgt cgacgcaatg aacttaacat tgcatttaca | 960 |
| tttgatctga ttcgtttgga tcgtaatgtc gaggaacgct ggcgtgaaaa agcctggtcc | 1020 |
| ctggttgatt ttcgccagac gatcggcaag gtagatcgtg cagccggaaa atacggctgg | 1080 |
| aacgcattct ttttggacaa ccacgacaac ccacgagctg tctcccactt cggcgatgac | 1140 |
| cggcctcaat ggcgccaggc gtctgcaaag gccctggcca ccctgattat cacccagagg | 1200 |
| gcgaccccgt ttatctacca gggctccgag ctgggcatga ctaattaccc tttcaagact | 1260 |
| atcgcggatt tcgatgacat tgaagtgaag ggttttttggc aggattatgt gagcagcggt | 1320 |
| cgagttgacc cagaggattt catgcgcaac gttcgtctaa ccagtcgcga caactcccgc | 1380 |
| acaccctttcc aatgggacga atcggccat gctggcttca cctccggcac gccctggttt | 1440 |
| aaggtgaacc ctaactataa gctcatcaat gcgtccgatc agatgaagga ttcagattcc | 1500 |
| gttttcaact actaccgcaa actcatccgc cttcgccacg ctattcctgc gttgacctac | 1560 |
| ggggagtata agatctgga tccatacaat gacaccgtct acgcatttac ccgcacccac | 1620 |
| ggtgacaagc gataccctggt cgtgatcaac tttaaagaga acaaagtcaa ctatcgtttg | 1680 |
| cccggtcagc ttagcattcg ccagactctg tccgagtcat cggcatccca acgtgtagcc | 1740 |
| gacaatgctc acgagttgct cctgcaacca tggcaatccg gtatctatag gctaaattga | 1800 |

<210> SEQ ID NO 31
<211> LENGTH: 1770
<212> TYPE: DNA
<213> ORGANISM: Artificial Sequence
<220> FEATURE:
<223> OTHER INFORMATION: aglA from Saccharomyces cerevisiae

<400> SEQUENCE: 31

| | |
|---|---|
| atgactattt cttctgcaca tccagagaca gaaccaaagt ggtggaaaga ggccacgttc | 60 |
| tatcaaattt acccagcaag tttcaaagac tctaatgacg atggctgggg tgacatgaaa | 120 |
| gggattgcct ccaagctgga gtacatcaaa gagcttggtg ccgatgccat ttggatctca | 180 |
| ccattctacg actcgccaca agatgatatg ggttacgata ttgccaacta cgaaaaggtc | 240 |
| tggccaacat atggtacgaa tgaagactgc tttgccttga tcgaaaagac acataagctt | 300 |
| ggtatgaaat ttatcaccga cttggtcatc aatcactgtt ccagcgaaca tgaatggttc | 360 |
| aaagagagca gatcctcgaa gactaatcca aagcgtgact ggttcttctg gagacctcct | 420 |
| aaaggttatg acgccgaagg caagccaatt cctccaaaca attggaaatc ctattttggt | 480 |
| ggttccgcat ggaccttcga tgaaagacaa caagaattct acttgcgttt gtttttgctcc | 540 |
| actcaacctg atttgaattg ggagaatgaa gactgtagaa aggcaatcta cgaaagtgcc | 600 |

-continued

```
gttggatact ggttagacca tggtgtagac ggctttagaa ttgatgtcgg aagtttgtac    660
tccaaagttg taggtttacc agatgctcct gttgttgaca aaaactcgac ttggcaatcc    720
agtgatccat acacattgaa tggaccacgt attcacgagt tccatcaaga aatgaatcaa    780
ttcatcagaa acagagtgaa ggatggcagg gagattatga cagttggtga aatgcaacat    840
gcctccgacg aaactaagag actttatacg agtgcttcaa gacacgaact tagtgagtta    900
tttaactttt cccacactga tgtggggact tcacctttgt tccgttacaa cttggtccca    960
tttgaactga aggattggaa gattgccctt gctgagctgt tcaggtacat taatggtaca   1020
gattgttggt caacaatcta tctggaaaat cacgaccaac ctcgttcaat tacgagattt   1080
ggtgacgatt ctcccaagaa ccgtgttatt tctggtaagt tactctctgt gttgctaagt   1140
gccttgaccg gtactctata tgtgtatcag ggacaagagc ttggccaaat caatttcaag   1200
aactggcctg ttgaaaagta cgaggatgtc gaaatcagaa acaactacaa tgccattaaa   1260
gaagagcatg gggaaaactc agaggagatg aaaaagtttt tagaagccat tgcccttatc   1320
tccagggacc atgctagaac acctatgcaa tggtctcgtg aggagccaaa tgctggtttt   1380
tctggtccta gtgctaaacc atggttttac ttgaacgact ctttcagaga aggcattaac   1440
gtcgaagatg aaatcaagga tcccaactcg gttttgaact tctggaagga ggccttgaag   1500
tttagaaagg cgcataaaga cattactgtg tacggatacg atttcgagtt tattgattta   1560
gacaataaga agttgtttag cttcacaaag aagtacaaca ataaaacatt gtttgcggct   1620
ttgaacttta gctctgatgc gacagatttc aagattccaa atgatgattc atcgttcaag   1680
ttagagtttg gaaactatcc aaagaaggag gtagatgcct cttccagaac attgaagcca   1740
tgggaaggaa gaatatatat cagcgaatga                                     1770
```

MICROORGANISM FOR PRODUCING L-AMINO ACID WITH ENHANCED ACTIVITY OF α-GLUCOSIDASE AND METHOD FOR PRODUCING L-AMINO ACID USING THE SAME

STATEMENT REGARDING SEQUENCE LISTING

The Sequence Listing associated with this application is provided in text format in lieu of a paper copy, and is hereby incorporated by reference into the specification. The name of the text file containing the Sequence Listing is 200187_451USPC_SEQUENCE_LISTING.txt. The text file is 27 KB, was created on Aug. 4, 2019, and is being submitted electronically via EFS-Web.

TECHNICAL FIELD

The present disclosure relates to a microorganism for producing an L-amino acid with enhanced activity of α-glucosidase and a method for producing an L-amino acid using the same.

BACKGROUND ART

L-Amino acids have been used in the animal feed, medicine, and cosmetics industries, and are mainly produced by fermentation using the genus *Corynebacterium* or the genus *Escherichia*. For the production of L-amino acids, various studies such as the development of highly efficient production strains and fermentation process technologies have been performed. Specifically, target material-specific approach methods, such as increasing expression of genes coding enzymes involved in L-amino acid biosynthesis or removing genes unnecessary for biosynthesis, have mainly been used (Korean Patent Registration No. 10-0838038).

Meanwhile, various studies for increasing sugar availability have been conducted to increase target substance productivity of a microorganism, and at the same time, there has been continuous demand for considering an efficient medium composition and microbial growth. For example, a technology has been reported for preparing a mutant microorganism capable of increasing availability of cellobiose through overexpression of ascB or chbF gene and using cellobiose and other sugars such as xylose, mannose, and galactose at the same time, and producing biofuel using the same (Korean Patent Registration No. 10-1484108). However, there is a need for continued studies on the correlation between the sugar availability and L-amino acid productivity of the microorganism.

DISCLOSURE

Technical Problem

The present inventors surprisingly verified an effect of improving a yield of an L-amino acid as a target substance without adding isomaltose and maltose as a result of introducing α-glucosidase, which is known to decompose isomaltose and maltose, to a strain of the genus *Corynebacterium*, thereby completing the present disclosure.

Technical Solution

An object of the present disclosure is to provide a microorganism of the genus *Corynebacterium* that produces an L-amino acid with enhanced activity of α-glucosidase.

Another object of the present disclosure is to provide a method for producing an L-amino acid comprising culturing the microorganism in a medium; and collecting an L-amino acid from the culture medium or microorganism.

Yet another object of the present disclosure is to provide a method for increasing production of an L-amino acid, including enhancing expression of α-glucosidase in a microorganism.

Still another object of the present disclosure is to provide a use of α-glucosidase for increasing production of an L-amino acid.

Advantageous Effects

According to the present disclosure, the microorganism of the genus *Corynebacterium* producing an L-amino acid has enhanced activity of α-glucosidase, thereby improving L-amino acid production yield. Therefore, the microorganism may be very usefully used for L-amino acid production.

BRIEF DESCRIPTION OF DRAWINGS

FIG. 1 illustrates an SDS-PAGE result of confirming expression of α-glucosidase in *Corynebacterium glutamicum* strains.

BEST MODE FOR INVENTION

Specifically, the present disclosure will be described as follows. Meanwhile, each description and embodiment disclosed in the present disclosure can also be applied to each other description and embodiment. That is, all combinations of the various components disclosed in the present disclosure belong to the scope of the present disclosure. In addition, the specific description described below may not limit the scope of the present disclosure.

In order to achieve the objects, an aspect of the present disclosure is a microorganism of the genus *Corynebacterium* that produces an L-amino acid with enhanced activity of α-glucosidase. The microorganism of the genus *Corynebacterium* of the present disclosure has enhanced activity of α-glucosidase to improve L-amino acid productivity. Accordingly, the microorganism of the genus *Corynebacterium* of the present disclosure may be very usefully used for L-amino acid production.

In the present disclosure, the term "α-glucosidase" is a kind of glucosidase for decomposing sugar into glucoses and refers to an enzyme having a characteristic of decomposing an α (1→4) bond. In the present disclosure, the α-glucosidase may be a protein having activity of α-glucosidase coded by an aglA gene, but so long as the α-glucosidase has activity corresponding to glucosidase which is enhanced in the microorganism of the genus *Corynebacterium* to improve the productivity of an L-amino acid, the type thereof is not particularly limited. The protein having the activity of α-glucosidase encoded by the aglA gene is known to have isomaltose or maltose decomposition activity (Glycobiology. 2010 November; 20(11)), and information on the α-glucosidase may be easily obtained by those skilled in the art through a known database (e.g., NCBI, UniProt, etc.). In the present disclosure, the α-glucosidase may be α-glucosidase derived from *Bifidobacterium adolescentis*, *Erwinia amylovora*, or *Saccharomyces cerevisiae*, and particularly, α-glucosidase derived from *Bifidobacterium adolescentis*, but is not limited thereto. The α-glucosidase derived from *Bifidobacterium adolescentis* described as an example of the present disclosure is not limited thereto, but may be a protein comprising an amino acid sequence of SEQ ID NO: 1. The α-glucosidase derived from *Erwinia amylovora* is not limited thereto, but may be a protein comprising an amino acid sequence of SEQ ID NO: 28. The α-glucosidase derived from *Saccharomyces cerevisiae* is not limited thereto, but may be a protein comprising an amino acid sequence of SEQ ID NO: 29. The protein comprising an amino acid sequence of SEQ ID NO: 1 may be used in a combination of a protein having an amino acid sequence of SEQ ID NO: 1 and a protein consisting of an amino acid sequence of SEQ ID NO: 1. Further, even if a 'protein or polypeptide comprising an amino acid sequence listed with a specific sequence number' is disclosed in the present disclosure, if a protein has an activity the same as or equivalent to that of the polypeptide comprising the amino acid sequence of the corresponding sequence number, it is apparent that proteins having an amino acid sequence which is partially deleted, modified, substituted, conservatively substituted, or added are also included in the scope of the present disclosure. For example, if the protein has an activity the same as or equivalent to that of the polypeptide comprising the amino acid sequence of the corresponding sequence number, it is apparent that addition of a sequence which does not modify a function of the protein before and after the amino acid sequence, naturally occurring mutation, silent mutation thereof, or conservative substitution are not excluded, and the sequence addition or mutation is included in the scope of the present disclosure. Further, if the protein has an activity the same as or equivalent to that of the polypeptide comprising the amino acid sequence of the corresponding sequence number, an amino acid sequence having homology or identity of 80% or more, particularly 90% or more, more particularly 95% or more, and much more particularly 99% or more with the amino acid sequence of the corresponding sequence number may be included in the scope of the present disclosure.

For example, the protein having activity of α-glucosidase in the present disclosure may be a protein comprising an amino acid sequence (SEQ ID NO: 1) of α-glucosidase derived from *Bifidobacterium adolescentis*, an amino acid sequence (SEQ ID NO: 28) of α-glucosidase derived from *Erwinia amylovora*, or an amino acid sequence (SEQ ID NO: 29) of α-glucosidase derived from *Saccharomyces cerevisiae*. If the α-glucosidase of the present disclosure is a protein that has an effect corresponding to α-glucosidase and enhances the activity in the microorganism of the genus *Corynebacterium* to improve productivity of an L-amino acid, it is apparent that the α-glucosidase is included in a protein having activity of α-glucosidase in the present disclosure. Particularly, as long as the α-glucosidase of the present disclosure has the activity of α-glucosidase and enhances the activity in the microorganism of the genus *Corynebacterium* to improve productivity of an L-amino acid, an amino acid sequence having homology or identity of 80% or more, particularly 90% or more, more particularly 95% or more, and much more particularly 99% or more with the amino acid sequence of SEQ ID NO: 1, SEQ ID NO: 28, or SEQ ID NO: 29 may be included in the scope of the present disclosure.

In the present disclosure, the term "homology or identity" means a degree associated with two given amino acid sequences or base sequences and may be represented as a percentage. Further, the homology and identity may often be used interchangeably.

The homology or identity of the conserved polynucleotide or polypeptide is determined by a standard array algorithm and a default gap penalty established by a used program may be used together. Substantially, a homologous or identical sequence may be generally hybridized under moderately or highly stringent conditions according to at least about 50%, 60%, 70%, 80%, or 90% of the entire sequence or the entire length. In the hybridized polynucleotide, a polynucleotide comprising a degenerate codon instead of a codon is also considered.

Whether any two polynucleotides or polypeptides have homology, similarity, or identity may be determined using a known computer algorithm such as the "FASTA" program using a default parameter, for example, in Pearson et al. (1988)[Proc. Natl. Acad. Sci. USA 85]: 2444. Alternatively, as performed in the Needleman program of the EMBOSS package (EMBOSS: The European Molecular Biology Open Software Suite, Rice et al., 2000, Trends Genet. 16: 276-277) (version 5.0.0 or subsequent version), the homology, similarity, or identity may be determined using the Needleman-Wunsch algorithm (Needleman and Wunsch, 1970, J. Mol. Biol. 48: 443-453) (including the GCG program package (Devereux, J., et al., Nucleic Acids Research 12: 387 (1984)), BLASTP, BLASTN, FASTA (Atschul, [S.] [F.,] [ET AL, J MOLEC BIOL 215]: 403 (1990); Guide to Huge Computers, Martin J. Bishop, [ED.,] Academic Press, San Diego,1994, and [CARILLO ETA/.](1988) SIAM J Applied Math 48: 1073). For example, the homology, similarity, or identity may be determined using BLAST or ClustalW of the National Center for Biotech Information Database.

The homology, similarity, or identity of the polynucleotide or polypeptide may be determined by comparing sequence information using a GAP computer program, for example, Needleman et al. (1970), J Mol Bio1.48:443. In summary, the GAP program is defined as a value obtained by dividing the number of similar arranged symbols (i.e., nucleotides or amino acids) by the entire number of symbols in the shorter of the two sequences. The default parameter for the GAP program may include (1) a unary numeral comparison matrix (containing values of 1 for identity and 0 for non-identity) and a weighted comparison matrix of Gribskov et al. (1986) Nucl. Acids Res. 14: 6745, as disclosed in Schwartz and Dayhoff, eds., Atlas Of Protein Sequence And Structure, National Biomedical Research Foundation, pp. 353-358 (1979) (alternatively, a substitution matrix of EDNAFULL (EMBOSS version of NCBI NUC4.4); (2) 3.0 penalty for each gap and additional 0.10 penalty for each symbol in each gap (alternatively, gap opening penalty 10, gap extension penalty 0.5); and (3) non-penalty for a terminal gap.

Accordingly, the term "homology" or "identity" used in the present disclosure represents relevance between sequences.

In the present disclosure, the term "conservative substitution" means substituting one amino acid with another amino acid having a similar structural and/or chemical property. The variation may have, for example, one or more conservative substitutions while still having one or more biological activities. Such an amino acid substitution may generally occur based on polarity, charge, solubility, and similarity in the hydrophobic, hydrophobic, and/or amphipathic nature of the residues. For example, positively charged (basic) amino acids include arginine, lysine, and histidine; negatively charged (acidic) amino acids include glutamic acid and aspartic acid; aromatic amino acids include phenylalanine, tryptophan, and tyrosine; and hydrophobic amino acids include alanine, valine, isoleucine, lysine, methionine, phenylalanine, tyrosine, and tryptophan.

Further, the polynucleotide sequence encoding the α-glucosidase may be a polynucleotide sequence encoding a protein which has activity of α-glucosidase and has enhanced activity in the microorganism of the genus *Corynebacterium* to improve productivity of an L-amino acid. For example, the polynucleotide sequence encoding the α-glucosidase may be a polynucleotide encoding *Bifidobacterium adolescentis*-derived α-glucosidase (SEQ ID NO: 1), *Erwinia amylovora*-derived α-glucosidase (SEQ ID NO: 28), and *Saccharomyces cerevisiae*-derived α-glucosidase (SEQ ID NO: 29). For example, the polynucleotide sequence may have a base sequence of SEQ ID NO: 2, a base sequence of SEQ ID NO: 30, and a base sequence of SEQ ID NO: 31, but the base sequence may be modified in an encoding region due to codon degeneracy. In addition, various modifications may be made in the encoding region in a range without changing the amino acid sequence by considering a codon preferred in an organism to express the base sequence. The polynucleotide sequence may be a polynucleotide including a polynucleotide sequence encoding the protein or a polynucleotide sequence having homology or identity of 80%, 90%, 95%, or 99% therewith. Further, if the polynucleotide sequence is a polynucleotide sequence encoding a protein which has the homology or identity and has an effect substantially identical or corresponding to the protein, it is apparent that a polynucleotide sequence which is partially deleted, modified, substituted, or added is included in the scope of the present disclosure.

Alternatively, a probe which may be prepared from a known gene sequence, for example, a sequence encoding a protein having activity of α-glucosidase of the present disclosure by hybridizing with a complementary sequence for the entire or a part of the polynucleotide sequence under stringent conditions may be included without limitation. The "stringent conditions" mean conditions which enable specific hybridization between polynucleotides. These conditions are specifically disclosed in the literature (e.g., Sambrook et al., Molecular Cloning, A Laboratory Manual, 2nd Edition, Cold Spring Harbor Laboratory press, Cold Spring Harbor, N.Y., 1989). For example, conditions of hybridizing genes having high homology, i.e., genes having homology of 80% or more, particularly 90% or more, more particularly 95% or more, and much more particularly 97% or more, and specifically particularly 99% or more and not hybridizing genes having low homology, or washing conditions of general Southern hybridization, which washing is performed once, particularly 2 to 3 times at salt concentration and temperature corresponding to 60° C., 1×SSC, 0.1% SDS, particularly 60° C., 0.1×SSC, 0.1% SDS, and more particularly 68° C., 0.1×SSC, 0.1% SDS may be included. The hybridization requires two polynucleotides to have a complementary sequence even if mismatch between bases is possible according to the stringent degree of hybridization. The term "complementary" is used to describe a relation between bases of polynucleotides which can be hybridized with each other. For example, for DNA, adenosine is complementary to thymine, and cytosine is complementary to guanine. Accordingly, the present disclosure may include isolated nucleotide segments complementary to the overall sequence as well as a substantially similar nucleotide sequence. Specifically, polynucleotides having homology use a hybridization condition that includes hybridization at a $T_m$ value of 55° C. and may be detected using the aforementioned conditions. In addition, the $T_m$ value may be 60° C., 63° C., or 65° C., but is not limited thereto and may be properly adjusted by those skilled in the art according to a purpose thereof. A proper stringent degree for hybridizing the polynucleotides depends on the length and the complementary degree of the polynucleotide and the variables are well known in the art (see Sambrook et al., supra, 9.50-9.51, 11.7-11.80).

In the present disclosure, the term "enhancement of activity" means that the activity is increased when an original microorganism is compared with the activity of a protein in a natural state or pre-mutant state, that is, endogenous activity, and is a concept including introduction of activity providing activity thereof by introducing the protein to a microorganism without the activity of a specific protein. The "endogenous activity" means an active state of a protein shown in a natural state or non-mutant state of the original microorganism.

Particularly, the "enhancement of activity" is not particularly limited thereto, but may include enhancing the activity by an increase in endogenous gene activity, endogenous gene amplification due to internal or external factors, introduction of genes from the outside, replacing or modifying of promoters, and an increase in enzyme activity by mutation as well as deriving an effect beyond its original function by enhancing activity of the protein itself. For example, the "enhancement of activity" may be performed by an increase in copy number in cells of genes encoding the protein, a method of modifying a gene expression regulatory sequence encoding the polypeptide, a method for modifying genes encoding the polypeptide on a chromosome by replacing genes encoding the polypeptide on the chromosome with mutant genes to enhance the activity of the polypeptide or inducing a mutation in genes on a chromosome encoding the polypeptide to enhance the activity of the polypeptide, and a method for introducing genes from the outside or inserting genes into the chromosome, but is not limited to these methods.

The increase in copy number of the genes is not specifically limited, but may be performed to be operably linked to a vector or to be inserted into a chromosome in a host cell. Specifically, the vector that is operably linked to the polynucleotide encoding the protein of the present disclosure and replicated and functioning regardless of the host may be introduced into the host cell. Alternatively, the vector which is operably linked to the polynucleotide to insert the polynucleotide into the chromosome in the host cell may be introduced into the chromosome of the host cell. The insertion into the chromosome of the polynucleotide may be performed by any method known in the art, for example, homologous recombination. Since the vector of the present disclosure may be inserted into the chromosome by the homologous recombination, the vector may further include a selection marker for confirming the insertion of the chromosome. The selection marker selects cells transformed by the vector to confirm insertion of a target polynucleotide, and markers may be used to provide selective phenotypes such as drug resistance, auxotrophy, resistance to cytotoxic drugs, or the expression of surface proteins, but are not limited thereto. In an environment treated with a selective agent, since only cells expressing the selection marker survive or represent different phenotypes of expression, transformed cells may be selected. The term "vector" in the present disclosure refers to a DNA construct comprising a polynucleotide sequence encoding a target peptide which is operably linked to a suitable expression regulatory sequence to express the target protein in a suitable host. The expression regulatory sequence includes a promoter capable of initiating transcription, any operator sequence for regulating such transcription, a sequence encoding a suitable mRNA ribosome-binding site, and a sequence for regulating the termination of transcription and translation, but is not limited thereto. The vector may be transformed into an appropriate host cell, and then may be replicated or function regardless of a host genome or integrated into the genome itself. The vector used in the present disclosure is not particularly limited, and any vector known in the art may be used. Examples of vectors to be generally used may include native or recombinant plasmids, cosmids, viruses, and bacteriophages. For example, as the phage vector or the cosmid vector, pWE15, M13, λMBL3, λMBL4, λIXII, λASHII, λAPII, λt10, λt11, Charon4A, Charon21A, and the like may be used, and as the plasmid vector, pDZ-based, pBR-based, pUC-based, pBluescriptll-based, pGEM-based, pTZ-based, pCL-based, and pET-based plasmids may be used.

In addition, the vector may comprise a polynucleotide sequence encoding a signal peptide. In the present disclosure, the term "signal peptide" refers to a protein in which the target protein may be secreted out of the cells and may be applied to be expressed in an integrated or separated state with the genes encoding the target protein. As long as the signal peptide in the present disclosure may be secreted out of the cells while maintaining the function of the target protein, the type thereof is not particularly limited. For example, in the present disclosure, CgR0949, NCgl2101, CgR1834, and ST2 (SEQ ID NOs. 14 to 17, respectively) may be used as examples of the signal peptide. Furthermore, a known proper signal peptide is selected by those skilled in the art to be used for secretion expression of α-glucosidase.

In the present disclosure, the term "transformation" refers to the introduction of a vector including a polynucleotide encoding a target protein into a host cell in such a way that the protein encoded by the polynucleotide is expressed in the host cell. As long as the transformed polynucleotide may be expressed in the host cell, all transformed polynucleotides are included regardless of whether the transformed polynucleotide is inserted and located in a chromosome of the host cell or located outside the chromosome. In addition, the polynucleotide includes DNA and RNA encoding the target protein. The polynucleotide may be introduced in any form as long as the polynucleotide may be introduced into a host cell and expressed. For example, the polynucleotide may be introduced into a host cell in a form of an expression cassette, which is a genomic structure including all elements required for self-expression. The expression cassette may generally include a promoter which is operably linked to the polynucleotide, a transcription termination signal, a ribosome-binding site, and a translation termination signal. The expression cassette may be a self-replicable expression vector. Further, the polynucleotide may also be introduced into the host cell as is and operably linked to a sequence required for expression in the host cell.

In addition, the term "operably linked" above means that the gene sequence is functionally linked to a promoter sequence, which initiates and mediates the transcription of the polynucleotide encoding the target peptide of the present disclosure.

Next, the modification of the expression regulatory sequence to increase the expression of the polynucleotide is not particularly limited thereto, but may be performed by inducing a sequence mutation by deletion, insertion, non-conservative or conservative substitution, or a combination thereof of a nucleic acid sequence to further enhance the activity of the expression regulatory sequence, or may be performed by replacement with a nucleic acid sequence having stronger activity. Specifically, the modification may be performed by replacement with a strong promoter. The expression regulatory sequence is not particularly limited thereto, but may include a promoter, an operator sequence, a sequence encoding a ribosome-binding site, a sequence regulating termination of transcription and translation, and the like.

Instead of an original promoter, a strong promoter may be linked to the upper portion of the polynucleotide expression unit, but is not limited thereto. Examples of known strong promoters may include cj1 to cj7 promoters (Korean Patent Registration No. 0620092), an sp11 1, 7, or 13 promoter (Korean Patent Registration No. 1783170), a PgapA promoter, a lac promoter, a trp promoter, a trc promoter, a tac promoter, a λ phage PR promoter, a PL promoter, and a tet promoter.

Further, the modification of the polynucleotide sequence on the chromosome is not particularly limited thereto, but may be performed by inducing a mutation on the expression regulatory sequence by deletion, insertion, non-conservative or conservative substitution, or a combination thereof of a nucleic acid sequence to further enhance the activity of the polynucleotide sequence, or may be performed by replacement with an improved polynucleotide sequence having stronger activity. However, it is not limited thereto.

In the enhancement of the protein activity, there is no activity of a corresponding protein, or the activity or concentration thereof may be generally increased to 1%, 10%, 25%, 50%, 75%, 100%, 150%, 200%, 300%, 400%, or 500%, up to 1000% or 2000% based on the activity or concentration in a wild-type protein or an initial microorganism strain, but is not limited thereto.

The microorganism of the genus *Corynebacterium* of the present disclosure has enhanced activity of α-glucosidase to improve L-amino acid productivity as described above. Accordingly, the microorganism of the genus *Corynebacterium* of the present disclosure may be used for L-amino acid production.

The term "L-amino acid" in the present disclosure means a basic constituting unit of a protein that forms the body of a living organism in which an amino group and a carboxyl group are linked to the same carbon atom. The L-amino acid may be at least one selected from the group consisting of, for example, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, and L-valine. Further, the L-amino acid may be, for example, an aspartic acid-derived L-amino acid in a biosynthesis pathway of the microorganism and may be an L-amino acid biosynthesized by using L-aspartic acid as a substrate or an intermediate. The aspartic acid-derived L-amino acid may be at least one selected from the group consisting of L-lysine, L-threonine, and L-isoleucine as a more detailed example, but not limited thereto.

In the present disclosure, the "microorganism that produces an L-amino acid" may be a microorganism capable of producing and accumulating an L-amino acid from carbon sources in a medium. The type of microorganism that produces an L-amino acid is not particularly limited, but may be microorganisms belonging to the genus *Enterobacter*, the genus *Escherichia*, the genus *Erwinia*, the genus *Serratia*, the genus *Pseudomonas*, the genus *Providencia*, the genus *Corynebacterium*, and the genus *Brevibacterium*. More specifically, the microorganism may be a microorganism belonging to the genus *Corynebacterium*. The "genus *Corynebacterium*" in the present disclosure may be specifically *Corynebacterium glutamicum*, *Corynebacterium ammoniagenes*, *Brevibacterium lactofermentum*, *Brevibac-* terium flavum, Corynebacterium thermoaminogenes, Corynebacterium efficiens, and the like, but is not necessarily limited thereto.

More specifically, the microorganism that produces the L-amino acid may be Corynebacterium glutamicum, but is not limited thereto.

The microorganism of the genus Corynebacterium with enhanced activity of α-glucosidase may produce an L-amino acid at higher yield of L-amino acid production than a microorganism before the activity of the protein is enhanced, that is, a non-modified microorganism.

Another aspect of the present disclosure is a method for producing an L-amino acid, comprising culturing a microorganism of the genus Corynebacterium that produces an L-amino acid with enhanced activity of α-glucosidase. The method for producing an L-amino acid may further include collecting an L-amino acid from the cultured medium or microorganism.

The microorganism with enhanced activity of α-glucosidase and the L-almino acid are as described above.

In the present disclosure, the term "culture" means growing the microorganism under a properly regulated environment condition. The culturing process of the present disclosure may be performed under proper medium and culture conditions which are known in the art. The culturing process may be easily adjusted and used by those skilled in the art according to a selected strain. Specifically, the culture may be batch, continuous, and fed-batch, but is not limited thereto.

A carbon source included in the medium may include sugars and carbohydrates such as glucose, sucrose, lactose, fructose, maltose, starch, and cellulose; oils and fats such as soybean oil, sunflower oil, castor oil, and coconut oil; fatty acids such as palmitic acid, stearic acid, and linoleic acid; alcohols such as glycerol and ethanol; and organic acids such as acetic acid. These materials may be used individually or as a mixture, but are not limited thereto. A nitrogen source included in the medium may include organic nitrogen sources, such as peptone, yeast extract, gravy, malt extract, corn sediment, and soybeans; and inorganic nitrogen sources such as urea, ammonium sulfate, ammonium chloride, ammonium phosphate, ammonium carbonate, and ammonium nitrate, and these nitrogen sources may be used alone or in combination. However, the sources are not limited thereto. A phosphorus source included in the medium may include potassium dihydrogen phosphate, dipotassium hydrogen phosphate, and corresponding sodium-containing salts, but is not limited thereto. Further, in the medium, metal salts such as magnesium sulfate or iron sulfate may be included, and amino acids, vitamins, and suitable precursors may be included. These media or precursors may be added to the culture in a batch or continuous form, but are not limited thereto.

During the culture, a compound such as ammonium hydroxide, potassium hydroxide, ammonia, phosphoric acid, and sulfuric acid is added to the culture by a proper method to adjust the pH of the culture. In addition, during the culture, production of foam may be inhibited by using an anti-foaming agent such as a fatty acid polyclinic ester. Further, oxygen or oxygen-containing gases may be injected into the culture to maintain an aerobic state of the culture, and gases may not be injected, or nitrogen, hydrogen, or carbon dioxide gas may be injected to maintain anaerobic and microaerobic states. The temperature of the culture may be generally 25° C. and 40° C. and particularly 27° C. to 35° C. The culture period may last until a desired output of useful materials is obtained, and may be particularly 10 to 100 hours. However, the present disclosure is not limited thereto.

According to the present disclosure, it is possible to collect and/or additionally purify an L-amino acid produced in the culturing step and to collect a desired L-amino acid from the medium using a proper method known in the art according to a culture method, for example, a batch, continuous, or fed-batch culture method, but the present disclosure is not limited thereto. For example, centrifugation, filtration, anion-exchange chromatography, crystallization, and HPLC may be used, and it is possible to collect a desired L-amino acid from a medium or microorganism cultured using a proper method known in the art.

Yet another aspect of the present disclosure provides a method for increasing production of an L-amino acid, including enhancing activity of α-glucosidase in a microorganism.

Still another aspect of the present disclosure provides a use of α-glucosidase for increasing production of an L-amino acid.

The 'increasing production of an L-amino acid' may mean that L-amino acid productivity is increased to produce an L-amino acid at a higher L-amino acid production yield than a microorganism before the activity of the protein is enhanced, that is, a non-modified microorganism.

MODE FOR INVENTION

Hereinafter, the present disclosure will be described in more detail with reference to Examples. However, these Examples are only illustrative of the present disclosure, and the scope of the present disclosure is not limited to these

EXAMPLES

Example 1

Preparation of Vector for introducing α-glucosidase Gene
In order to confirm an effect of aglA gene of α-glucosidase, for example, a vector for inserting Bifidobacterium adolescentis-derived aglA gene (SEQ ID NO: 2) into a chromosome of a Corynebacterium glutamicum strain was prepared.

In order to amplify a Corynebacterium glutamicum-derived PgapA promoter, a promoter (SEQ ID NO: 3) designed to insert an EcoRI restriction enzyme site into a 5' terminus of the PgapA promoter and a primer (SEQ ID NO: 4) designed to insert an NdeI restriction enzyme site into a 3' terminus were synthesized. As a result, PgapA promoter DNA fragments including the EcoRI restriction enzyme site at the 5' terminus and the NdeI restriction enzyme site at the 3' terminus were obtained. In a PCR condition, after denaturation at 94° C. for 5 minutes, denaturation at 94° C. for 30 seconds, annealing at 56° C. for 30 seconds, and polymerization at 72° C. for 30 seconds were repeated 30 times, and then polymerization was performed at 72° C. for 7 minutes.

Primer for Amplifying PgapA Promoter

```
Forward:
                                    (SEQ ID NO: 3)
5'-TCAGAATTCTTGGGATTACCATTGAAGCC-3'

Backward:
                                    (SEQ ID NO: 4)
5'-TCACATATGGTGTCTCCTCTAAAGATTGT-3'
```

In order to amplify ORF of Bifidobacterium adolescentis-derived aglA gene based on a reported base sequence, primers (SEQ ID NOs. 5 to 8) designed to insert an NdeI restriction enzyme site and a signal peptide for protein secretion to an initiation codon position and a primer (SEQ ID NO: 9) designed so that a SpeI restriction enzyme site is included in the bottom of a termination codon were synthesized.

The signal peptide is a protein that helps, for example, an AglA enzyme to be released outside the cells, and 4 types (SEQ ID NOs. 14 to 17) were selected and tested. The primer sequences and amino acid sequences of the signal peptide are as follows (Table 1).

TABLE 1

| Primer for amplifying aglA ORF | Including SP1 Forward | 5'-TCA<u>CATATG</u>caaataaaccg ccgaggcttcttaaaagccaccg caggacttgccactatcggcgct gccagcatgtttatgccaaaggc caacgcccttggagcaACGAATT TCAATCGTTCCA-3' (SEQ ID NO: 5) |
|---|---|---|
| | Including SP2 Forward | 5'-TCA<u>CATATG</u>CATTCAAAGGA AGAGTTAACAGTGCGTAAAGGAA TTTCCCGCGTCCTCTCGGTAGCG GTTGCTAGTTCAATCGGATTCGG AACTGTACTGACAGGCACCGGCA TCGCAGCAGCTCAAGACACGAAT TTCAATCGTTCCA-3' (SEQ ID NO: 6) |
| | Including SP3 Forward | 5'-TCA<u>CATATG</u>CGTAAGTTCCG CAATACTGCAATCGCACTGGTTT CAGCTGCTGCTATCTCCCTCGGT GGAGTTACTGCTGCAACCGCTCA GGAAGCTACGAATTTCAATCGTT CCA-3' (SEQ ID NO: 7) |
| | Including SP4 Forward | 5'-TCA<u>CATATG</u>AAAAAGAATAT CGCATTTCTTCTTGCATCTATGT TCGTTTTTTCTATTGCTACAAAC GCGTACGCTACGAATTTCAATCG TTCCA-3' (SEQ ID NO: 8) |
| | Backward | 5'-TCA<u>ACTAGT</u>TCAGAGCTGAA TCACGACTC-3' (SEQ ID NO: 9) |
| Primer for amplifying malL ORF | Including SP3 Forward | 5'-TCA<u>CATATG</u>CGTAAGTTCCG CAATACTGCAATCGCACTGGTTT CAGCTGCTGCTATCTCCCTCGGT GGAGTTACTGCTGCAACCGCTCA GGAAGCTTCAGGCATCAAACTTT CTTC-3' (SEQ ID NO: 10) |
| | Backward | 5'-TCA<u>ACTAGT</u>TCAATTTAGCC TATAGATAC-3' (SEQ ID NO: 11) |
| Primer for amplifying Ima1 ORF | Including SP3 Forward | 5'-TCA<u>CATATG</u>CGTAAGTTCCG CAATACTGCAATCGCACTGGTTT CAGCTGCTGCTATCTCCCTCGGT GGAGTTACTGCTGCAACCGCTCA GGAAGCTACTATTTCTTCTGCAC ATCC-3' (SEQ ID NO: 12) |
| | Backward | 5'-TCA<u>ACTAGT</u>TCATTCGCTGA TATATATTCTT-3' (SEQ ID NO: 13) |
| Signal peptide | SP1 CgR0949 | MQINRRGFLKATAGLATIGAASM FMPKANALGA (SEQ ID NO: 14) |
| | SP2 NCgl2101 | MHSKEELTVRKGISRVLSVAVAS SIGFGTVLTGTGIAAAQD (SEQ ID NO: 15) |

TABLE 1-continued

| SP3 | CgR1834 | MRKFRNTAIALVSAAAISLGGVT AATAQEA (SEQ ID NO: 16) |
|---|---|---|
| SP4 | ST2 | MKKNIAFLLASMFVFSIATNAYA (SEQ ID NO: 17) |

An aglA ORF fragment including an NdeI restriction enzyme site and each signal peptide at a 5' terminus and a SpeI restriction enzyme site at a 3' terminus was obtained by using genomic DNA of *Bifidobacterium adolescentis* as a template. In a PCR condition, after denaturation at 94° C. for 5 minutes, denaturation at 94° C. for 30 seconds, annealing at 56° C. for 30 seconds, and polymerization at 72° C. for 2 minutes were repeated 30 times, and then polymerization was performed at 72° C. for 7 minutes.

After the four PCR amplification products were treated with restriction enzymes included at both ends, a pDZ vector (Korean Patent Registration No. 10-0924065) was treated with restriction enzymes EcoRI and SalI to be linked to the obtained DNA fragment to prepare pDZ-PgapA-SP1-aglA (B.al), pDZ-PgapA-SP2-aglA(B. al), pDZ-PgapA-SP3-aglA (B.al), and pDZ-PgapA-SP4-aglA(B.al) vectors. Further, in order to prepare another microorganism with enhanced activity of α-glucosidase, the following strain-derived α-glucosidase genes were secured. Particularly, malL and Ima1 ORF fragments including an NdeI restriction enzyme site and each signal peptide at a 5' terminus and a SpeI restriction enzyme site at a 3' terminus were obtained by using an EAMY 1858 (malL) genome of *Erwinia amylovora* CFBP1430 and IMA1 genomic DNA of *Saccharomyces cerevisiae* as templates. In a PCR condition, after denaturation at 94° C. for 5 minutes, denaturation at 94° C. for 30 seconds, annealing at 56° C. for 30 seconds, and polymerization at 72° C. for 2 minutes were repeated 30 times, and then polymerization was performed at 72° C. for 7 minutes.

After the two PCR amplification products were treated with restriction enzymes included at both ends, a pDZ vector (Korean Patent Registration No. 10-0924065) was treated with restriction enzymes EcoRI and SalI to be linked to the obtained DNA fragments to prepare pDZ-PgapA-SP3-malL (E.am) and pDZ-PgapA-SP3-Ima1(S.ce) vectors.

Example 2

Preparation of Microorganism introducing α-glucosidase

In order to introduce a gene encoding α-glucosidase to a *Corynebacterium glutamicum* strain, 6 vectors prepared in Example 1 were transformed into a *Corynebacterium glutamicum* lysine-producing strain KCCM11016P (the microorganism was published as KFCC10881 and then re-deposited to an International Depositary Authority under the Budapest Treaty to receive deposit number KCCM11016P, in Korean Patent Registration No. 10-0159812) by an electric pulse method (Van der Rest et al., Appl. Microbiol. Biotechnol. 52:541-545, 1999) and colonies in which each gene was introduced by homologous chromosome recombination were screened. In order to screen the colonies by a PCR method, primers of SEQ ID NOs. 18 and 19 were used.

Primer for Identifying AglA Gene Transfer

Forward: (SEQ ID NO: 18)
5'-GACCATTTATTCGCAACTGTG-3'

-continued

Backward:
(SEQ ID NO. 19)
5'-TCTGCAAGGCGTTCGGAATT-3'

The transformed strains were called KCCM11016P::PgapA-SP1-aglA(B.al), KCCM11016P::PgapA-SP2-aglA(B.al), KCCM11016P::PgapA-SP3-aglA(B.al) KCCM11016P::PgapA-SP4-aglA(B. al), KCCM11016P::PgapA-SP3-malL(E.am), and KCCM11016P::PgapA-SP3-Ima1 (S.ce).

Example 3

Confirmation of Protein Expression of Lysine-Producing Microorganism Introducing α-glucosidase A mother strain *Corynebacterium glutamicum* KCCM11016P was used as a control group, and 6 types of KCCM11016P::PgapA-SP1-aglA(B.al), KCCM11016P::PgapA-SP2-aglA(B.al), KCCM11016P::PgapA-SP3-aglA(B.al) KCCM11016P::PgapA-SP4A-aglA(B.al), KCCM11016P::PgapA-SP3-malL(E.am), and KCCM11016P::PgapA-SP3-Ima1(S.ce) prepared in Example 2 were cultured by a method illustrated in the following Example 4 and then centrifuged at high speed to obtain a supernatant. The expression of an α-glucosidase enzyme in a culture medium was measured by an SDS-PAGE method using a part of the obtained supernatant. As a result, a protein expressed in a 70 kDa position was confirmed (FIG. 1).

Example 4

Evaluation of L-amino Acid Productivity of Lysine-Producing Microorganism Introducing α-glucosidase A mother strain *Corynebacterium glutamicum* KCCM11016P was used as a control group, and 6 types of KCCM11016P::PgapA-SP1-aglA(B.al), KCCM11016P::PgapA-SP2-aglA(B.al), KCCM11016P::PgapA-SP3-aglA(B.al) KCCM11016P::PgapA-SP4-aglA(B.al), KCCM11016P::PgapA-SP3-malL(E.am), and KCCM11016P::PgapA-SP3-Ima1(S.ce) prepared in Example 2 were cultured by the following method for a predetermined time, and then a lysine concentration was measured. The results were illustrated in Table 2. First, each strain was inoculated in a 250 mL corner-baffle flask containing a 25 mL seed medium, and shake-cultured at 30° C. for 20 hours at 200 rpm. Thereafter, 1 mL of a seed culture solution was inoculated in a 250 mL corner-baffle flask containing 24 mL of a production medium and shake-cultured at 32° C. for 72 hours at 200 rpm. Compositions of the seed medium and the production medium were as follows. After the culture was terminated, a concentration of L-lysine was measured by HPLC (Waters 2478).

<Seed Medium (pH 7.0)>20 g of glucose, 10 g of peptone, 5 g of yeast extract, 1.5 g of urea, 4 g of $KH_2PO_4$, 8 g of $K_2HPO_4$, 0.5 g of $MgSO_4 \cdot 7H_2O$, 100 μg of biotin, 1000 μg of thiamine.HCl, 2000 μg of calcium pantothenate, and 2000 μg of nicotine (based on 1 L of distilled water) <Production Medium (pH 7.0)>

100 g of glucose, 40 g of $(NH_4)_2SO_4$, 2.5 g of soybean protein, 5 g of corn steep solids, 3 g of urea, 1 g of $KH_2PO_4$, 0.5 g of $MgSO_4 \cdot 7H_2O$, 100 μg of biotin, 1000 μg of thiamine.HCl, 2000 μg of calcium pantothenate, 3000 μg of nicotinamide, and 30 g of $CaCO_3$ (based on 1 L of distilled water)

TABLE 2

| Strain | No. | Lysine concentration (g/L) | Lysine mean concentration (g/L) |
|---|---|---|---|
| KCCM11016P | 1 | 36.6 | 36.8 |
|  | 2 | 36.4 |  |
|  | 3 | 37.5 |  |
| KCCM11016P::PgapA-SP1-aglA(*B.al*) | 1 | 40.0 | 39.1 |
|  | 2 | 38.5 |  |
|  | 3 | 38.9 |  |
| KCCM11016P::PgapA-SP2-aglA(*B.al*) | 1 | 39.0 | 38.7 |
|  | 2 | 38.4 |  |
|  | 3 | 38.7 |  |
| KCCM11016P::PgapA-SP3-aglA(*B.al*) | 1 | 39.8 | 40.4 |
|  | 2 | 41.9 |  |
|  | 3 | 39.5 |  |
| KCCM11016P::PgapA-SP4-aglA(*B.al*) | 1 | 39.3 | 38.8 |
|  | 2 | 38.5 |  |
|  | 3 | 38.6 |  |
| KCCM11016P::PgapA-SP3-malL(*E.am*) | 1 | 38.1 | 38.4 |
|  | 2 | 38.5 |  |
|  | 3 | 38.6 |  |
| KCCM11016P::PgapA-SP3-imal(S.ce) | 1 | 37.9 | 38.0 |
|  | 2 | 38.1 |  |
|  | 3 | 38.1 |  |

From the results, it could be seen that in all six types of lysine-producing strains with the introduction of α-glucosidase expression ability, lysine productivity was increased compared to a control group. In particular, in KCCM11016P::PgapA-SP3-aglA(B.al), the highest increase in productivity was shown. In the culture of the microorganism, it is a very meaningful result that the productivity of lysine was increased by at least 3.2% and up to 9.7% due to activity regulation of genes other than biosynthesis pathways. In addition, the effects of enhancing L-amino acid productivity by increasing the activity of α-glucosidase in the present disclosure were verified by confirming that the L-amino acid productivity was increased without the addition of isomaltose and maltose in the medium, which were expected to be used as a substrate by α-glucosidase. From the results, in the case of using appropriate signal peptides by selection of those skilled in the art, it is expected that a higher increase rate will be shown.

The prepared KCCM11016P::PgapA-SP2-aglA(B.al) was called *Corynebacterium glutamicum* CA01-7523 and deposited in the Korean Culture Center of Microorganisms (KCCM) as an International Depositary Authority under the Budapest Treaty on Mar. 5, 2018, to receive accession number KCCM12228P.

Example 5

Preparation of CJ3P Strain Introduced with α-glucosidase and Analysis of Lysine Productivity In order to confirm whether the same effect would be shown even in another *Corynebacterium glutamicum* strain producing L-lysine, PgapA-SP3-aglA(B.al) was introduced to a *Corynebacterium glutamicum* CJ3P (Binder et al. Genome Biology 2012, 13:R40) strain having L-lysine productivity in the same manner as in Example 2 by introducing 3 types of variants [pyc(P458S), hom(V59A), lysC (T311I)] to a wild-type *Corynebacterium glutamicum* ATCC13032 strain to prepare a strain introduced with α-glucosidase. The prepared strain was called CJ3P::PgapA-SP3-aglA(B.al). The CJ3P strain as a control group and the CJ3P::PgapA-SP3-aglA(B.al) were cultured in the same manner as in Example 4, and lysine productivity was analyzed and illustrated in Table 3 below.

TABLE 3

Lysine Productivity Analysis

| Strain | No. | Lysine concentration (g/L) | Lysine mean concentration (g/L) |
|---|---|---|---|
| CJ3P | 1 | 8.0 | 8.0 |
|  | 2 | 7.6 |  |
|  | 3 | 8.4 |  |
| CJ3P::PgapA-SP3-aglA(*B.al*) | 1 | 8.6 | 8.7 |
|  | 2 | 8.3 |  |
|  | 3 | 9.1 |  |

From the result of analyzing the lysine concentration, it was confirmed that lysine yield was increased in the strain introduced with α-glucosidase. In addition, in the culture of microorganisms, it is a very meaningful result that the productivity of lysine was increased by 8.8% due to activity regulation of genes other than biosynthesis pathways. Further, in the case of using appropriate signal peptides by selection of those skilled in the art, it is expected that a higher increase rate will be shown.

Example 6

Preparation of Threonine-Producing Strain Introduced with α-glucosidase and Analysis of Threonine Productivity In order to clearly confirm a change in L-threonine productivity by introduction of α-glucosidase, a variant was introduced to a gene encoding homoserine dehydrogenase producing homoserine, which is a common intermediate of the biosynthesis pathways of L-threonine and L-isoleucine, and enhanced. Specifically, a known hom(G378E) variant (R. Winkels, S. et al., Appl. Microbiol. Biotechnol. 45, 612-620, 1996) was introduced to the CJ3P:: PgapA-SP3-aglA(B.al) strain used in Example 5 to prepare a strain. Further, a strain in which the hom(G378E) variant was introduced to a control CJ3P was prepared. A recombinant vector for variant introduction was prepared by the following method.

In order to prepare a vector introduced with hom(G378E), first, primers (SEQ ID NOs. 20 and 21) were synthesized in which a restriction enzyme XbaI recognition site was inserted into a 5' fragment and a 3' fragment at positions about 600 bp upstream and downstream of positions 1131 to 1134 of hom gene by using genomic DNA extracted from a wild-type *Corynebacterium glutamicum* ATCC13032 strain as a template. Further, primers (SEQ ID NOs. 22 and 23) for substituting a base sequence of the hom gene were synthesized. A pDZ-hom(G378E) plasmid was prepared so that DNA fragments (600 bp each) located at 5' and 3' termini of the hom gene were linked to the pDZ vector (Korean Patent Registration No. 10-0924065).

Primer for Inserting XbaI Recognition Site

5' fragment:

(SEQ ID NO: 20)
5'-TCCTCTAGACTGGTCGCCTGATGTTCTAC-3'

3' fragment:

(SEQ ID NO: 21)
5'-GACTCTAGATTAGTCCCTTTCGAGGCGGA-3'

Primer for Substituting Hom Gene (SEQ ID NO: 22)
5'-GCCAAAACCTCCACGCGATC-3'

(SEQ ID NO: 23)
5'-ATCGCGTGGAGGTTTTGGCT-3'

A 5' terminal gene fragment was prepared through PCR using primers (SEQ ID NOs. 20 and 22) by using a chromosome of a wild-type strain as a template. In a PCR condition, after denaturation at 94° C. for 2 minutes, denaturation at 94° C. for 1 minute, annealing at 56° C. for 1 minute, and polymerization at 72° C. for 40 seconds were repeated 30 times, and then polymerization was performed at 72° C. for 10 minutes. In the same manner, a gene fragment at a 3' terminus of the hom gene was prepared through PCR using primers (SEQ ID NOs. 21 and 23). The amplified DNA fragments were purified using a PCR Purification kit from Quiagen Corporation and then used as insertion DNA fragments for preparing a vector. Meanwhile, a pDZ vector treated with a restriction enzyme XbaI and heated at 65° C. for 20 minutes and the insertion DNA fragment amplified through PCR were linked with each other using an Infusion Cloning Kit and then transformed to *E. coli* DH5a and smeared on an LB solid medium containing kanamycin (25 mg/L). Colonies transformed by a vector inserted with a target gene through PCR using primers of SEQ ID NOs. 20 and 21 were screened, and then a plasmid was obtained by a commonly known plasmid extraction method to prepare a vector pDZ-hom (G378E) for introducing a base substitution mutant of hom(G378E) into a chromosome.

Thereafter, the prepared pDZ-hom(G378E) vector was introduced to CJ3P and CJ3P::PgapA-SP3-aglA(B.al) strains in the same manner as in Example 2 to obtain CJ3P::hom(G378E) and CJ3P::PgapA-SP3-aglA(B.al)-hom (G378E) strains.

The two obtained strains were cultured in the same manner as in Example 4, and the threonine production concentration was analyzed and illustrated in Table 4 below.

TABLE 4

Threonine production concentration

| Strain | No. | Thr concentration (g/L) | Thr mean concentration (g/L) |
|---|---|---|---|
| CJ3P::hom(G378E) | 1 | 1.1 | 1.23 |
|  | 2 | 1.5 |  |
|  | 3 | 1.1 |  |
| CJ3P::PgapA-SP3-aglA(*B.al*)-hom(G378E) | 1 | 1.4 | 1.60 |
|  | 2 | 1.8 |  |
|  | 3 | 1.6 |  |

From the result of analyzing the threonine concentration, it was confirmed that the threonine concentration was increased in the strain introduced with α-glucosidase. In the culture of microorganisms, it is a very meaningful result that the productivity of threonine was increased by 30% due to activity regulation of genes other than biosynthesis pathways. Further, in the case of using appropriate signal peptides by selection of those skilled in the art, it is expected that a higher increase rate will be shown.

Example 7

Preparation of Isoleucine-Producing Strain Introduced with α-glucosidase and Analysis of Isoleucine Productivity In order to confirm an effect on L-isoleucine productivity by introduction of α-glucosidase, a variant was introduced to a gene encoding known L-threonine dehydratase and enhanced. Specifically, a known ilvA(V323A) variant (S. Morbach et al., Appl. Enviro. Microbiol., 62(12): 4345-4351, 1996) was introduced to the CJ3P::PgapA-SP3-aglA (B.al)-hom(G378E) strain used in Example 6 to prepare a strain. Further, a strain in which the ilvA(V323A) variant was introduced to a control CJ3P::hom(G378E) was prepared. A recombinant vector for variant introduction was prepared by the following method.

In order to prepare a vector introduced with ilvA(V323A), first, primers were synthesized (SEQ ID NOs. 24 and 25) in which a restriction enzyme XbaI recognition site was inserted into a 5' fragment and a 3' fragment at positions about 600 bp upstream and downstream of positions 966 to 969 of hom gene by using genomic DNA extracted from a wild-type Corynebacterium glutamicum ATCC13032 strain as a template. Further, primers (SEQ ID NOs. 26 and 27) for substituting a base sequence of the ilvA gene were synthesized. A pDZ-ilvA(V323A) plasmid was prepared so that DNA fragments (600 bp each) located at 5' and 3' termini of the ilvA gene were linked to the pDZ vector (Korean Patent Registration No. 10-0924065).

Primer for Inserting XbaI Recognition Site

```
5' fragment:
                                        (SEQ ID NO: 24)
5'-ACGGATCCCAGACTCCAAAGCAAAAGCG-3'

3' fragment:
                                        (SEQ ID NO: 25)
5'-ACGGATCCAACCAAACTTGCTCACACTC-3'
```

Primer for Substituting ilvA Gene

```
                                        (SEQ ID NO: 26)
5'-ACACCACGGCAGAACCAGGTGCAAAGGACA-3'

(SEQ ID NO: 27)
5'-CTGGTTCTGCCGTGGTGTGCATCATCTCTG-3'
```

A 5' terminal gene fragment was prepared through PCR using primers (SEQ ID NOs. 24 and 26) by using a chromosome of a wild-type strain as a template. In a PCR condition, after denaturation at 94° C. for 2 minutes, denaturation at 94° C. for 1 minute, annealing at 56° C. for 1 minute, and polymerization at 72° C. for 40 seconds were repeated 30 times, and then polymerization was performed at 72° C. for 10 minutes. In the same manner, a gene fragment at a 3' terminus of the ilvA gene was prepared through PCR using primers (SEQ ID NOs. 25 and 27). The amplified DNA fragments were purified using a PCR Purification kit from Quiagen Corporation and then used as insertion DNA fragments for preparing a vector. Meanwhile, a pDZ vector treated with a restriction enzyme XbaI and heated at 65° C. for 20 minutes and the insertion DNA fragment amplified through PCR were linked with each other using an Infusion Cloning Kit and then transformed to E. coli DH5a and smeared on an LB solid medium containing kanamycin (25 mg/L). Colonies transformed by a vector inserted with a target gene through PCR using primers of SEQ ID NOs. 24 and 25 were screened, and then a plasmid was obtained by a commonly known plasmid extraction method to prepare a vector pDZ-ilvA(V323A) for introducing a base substitution mutant of ilvA(V323A) into a chromosome.

Thereafter, the prepared pDZ-ilvA(V323A) vector was introduced to CJ3P::hom(G378E) and CJ3P::PgapA-SP3-aglA(B.al)-hom(G378E) strains in the same manner as in Example 2 to obtain CJ3P::hom(G378E)-ilvA(V323A) and CJ3P::PgapA-SP3-aglA(B. al)-hom(G378E)-ilvA(V323A) strains. The two obtained strains were cultured in the same manner as in Example 4, and the isoleucine production concentration was analyzed and illustrated in Table 5 below.

TABLE 5

| | Isoleucine production concentration | | |
|---|---|---|---|
| Strain | No. | Ile concentration (g/L) | Ile mean concentration (g/L) |
| CJ3P::hom(G378E)-ilvA(V323A) | 1 | 0.12 | 0.10 |
| | 2 | 0.10 | |
| | 3 | 0.09 | |
| CJ3P::PgapA-SP3-aglA(*B.al*)-hom(G378E)-ilvA(V323A) | 1 | 0.15 | 0.13 |
| | 2 | 0.11 | |
| | 3 | 0.13 | |

As shown in the results of Table 5, it was confirmed that the isoleucine concentration was increased in the strain introduced with α-glucosidase. In the culture of microorganisms, it is a very meaningful result that the productivity of isoleucine was increased by 30% due to activity regulation of genes other than biosynthesis pathways. Further, in the case of using appropriate signal peptides by selection of those skilled in the art, it is expected that a higher increase rate will be shown.

It will be appreciated by those skilled in the art that the present disclosure as described above may be implemented in other specific forms without departing from the technical spirit thereof or essential characteristics. Thus, it is to be appreciated that embodiments described above are intended to be illustrative in every sense, and not restrictive. The scope of the present disclosure is represented by the claims to be described below rather than the detailed description, and it is to be interpreted that the meaning and scope of the claims and all changes or modified forms derived from the equivalents thereof come within the scope of the present disclosure.

The invention claimed is:

1. A microorganism of the genus *Corynebacterium* that produces an L-amino acid, wherein said microorganism has been genetically modified to express the *Bifidobacterium adolescentis* aglA protein.

2. The microorganism of claim 1, wherein the aglA protein is encoded by the aglA gene of SEQ ID NO: 2.

3. The microorganism of claim 1, wherein the aglA protein consists of an amino acid sequence of SEQ ID NO: 1.

4. The microorganism of claim 1, wherein the L-amino acid is at least one selected from the group consisting of L-lysine, L-threonine, and L-isoleucine.

5. The microorganism of claim 1, wherein the microorganism of the genus *Corynebacterium* is *Corynebacterium glutamicum*.

6. A method for producing an L-amino acid, comprising:
  culturing a microorganism of the genus *Corynebacterium* that produces an L-amino acid, wherein said microorganism has been genetically modified to express the *Bifidobacterium adolescentis* aglA protein in a medium; and
  collecting the L-amino acid from the cultured medium or microorganism.

7. The method for producing the L-amino acid of claim 6, wherein the aglA protein is encoded by the aglA gene of SEQ ID NO: 2.

8. The method for producing the L-amino acid of claim 6, wherein the aglA protein consists of an amino acid sequence of SEQ ID NO: 1.

9. The method for producing the L-amino acid of claim 6, wherein the L-amino acid is at least one selected from the group consisting of L-lysine, L-threonine, and L-isoleucine.

* * * * *